(12) United States Patent
Fisher

(10) Patent No.: US 10,241,032 B2
(45) Date of Patent: Mar. 26, 2019

(54) IMPELLER BLADE FOR CALIBRATING LIGHT SENSOR

(71) Applicant: HEWLETT-PACKARD INDIGO B.V., Amstelveen (NL)

(72) Inventor: Gil Fisher, Shoham (IL)

(73) Assignee: HP Indigo B.V., Amstelveen (NL)

( * ) Notice: Subject to any disclaimer, the term of this patent is extended or adjusted under 35 U.S.C. 154(b) by 0 days.

(21) Appl. No.: 15/540,530

(22) PCT Filed: Jan. 23, 2015

(86) PCT No.: PCT/EP2015/000127
§ 371 (c)(1),
(2) Date: Jun. 28, 2017

(87) PCT Pub. No.: WO2016/116116
PCT Pub. Date: Jul. 28, 2016

(65) Prior Publication Data
US 2018/0003620 A1 Jan. 4, 2018

(51) Int. Cl.
| | | |
|---|---|---|
| *G01N 21/27* | (2006.01) | |
| *G01N 21/59* | (2006.01) | |
| G01N 21/85 | (2006.01) | |
| G01F 1/06 | (2006.01) | |

(52) U.S. Cl.
CPC .......... *G01N 21/276* (2013.01); *G01N 21/59* (2013.01); *G01F 1/065* (2013.01); *G01N 21/85* (2013.01)

(58) Field of Classification Search
CPC combination set(s) only.
See application file for complete search history.

(56) References Cited

U.S. PATENT DOCUMENTS

| | | |
|---|---|---|
| 4,013,953 A | 3/1977 | Skala |
| 5,241,189 A | 8/1993 | Vandagriff et al. |
| 5,638,174 A * | 6/1997 | Henderson ................ G01F 1/06 356/338 |
| 5,815,768 A | 9/1998 | Clifton |
| 7,359,055 B2 | 4/2008 | Schneider |

(Continued)

FOREIGN PATENT DOCUMENTS

| | | |
|---|---|---|
| EP | 0682232 | 11/1995 |
| GB | 2083210 | 3/1982 |
| JP | S5529780 | 3/1980 |

OTHER PUBLICATIONS

Jeong, J., Understanding Optical Power Measurements, (Jun. 25, 2012) http://www.electronicdesign.com/energy/understanding-optical-power-measurements.

*Primary Examiner* — Tri T Ton
(74) *Attorney, Agent, or Firm* — HP Inc. Patent Department

(57) ABSTRACT

In some examples, an apparatus can include a light transmitter, a light sensor aligned along a light transmittance axis of the light transmitter, an impeller positioned between the light transmitter and the light sensor. The impeller can in some examples include a blade to pass through the light transmittance axis during rotation of the impeller. The blade can in some examples be translucent to permit calibration of the light sensor based on a comparison of a first light sensor reading when the blade intersects the light transmittance axis and a second light sensor reading when the blade does not intersect the light transmittance axis.

12 Claims, 13 Drawing Sheets

(56) References Cited

U.S. PATENT DOCUMENTS

| | | |
|---|---|---|
| 2007/0115314 A1 | 5/2007 | Kondo et al. |
| 2009/0114675 A1* | 5/2009 | Kuzar .................. B67D 3/0006 |
| | | 222/40 |
| 2012/0320378 A1* | 12/2012 | Shemer ................ G01N 21/274 |
| | | 356/434 |
| 2013/0140446 A1* | 6/2013 | Benner, Jr. ............... G01D 5/34 |
| | | 250/231.16 |

* cited by examiner

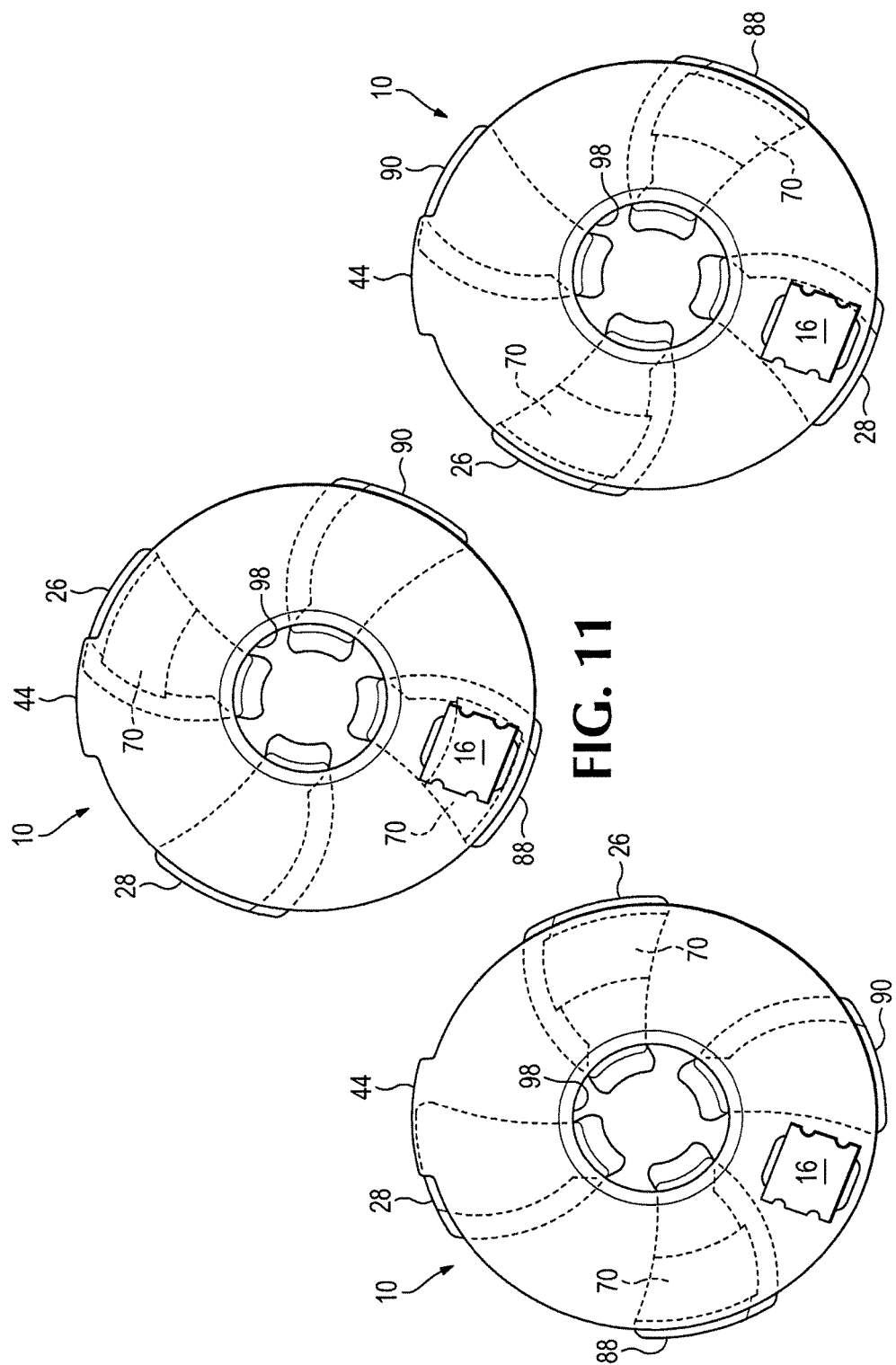

IMPELLER BLADE FOR CALIBRATING LIGHT SENSOR

CROSS-REFERENCE TO RELATED APPLICATION

This application is a U.S. National Stage Application of and claims priority to International Patent Application No. PCT/EP2015/000127, filed on Jan. 23, 2015, and entitled "IMPELLER BLADE FOR CALIBRATING LIGHT SENSOR".

BACKGROUND

Sensors are often used to measure properties of printer fluid within a printer fluid tank or other receptacle. Such sensors can, for example, include temperature sensors to measure a temperature of the printer fluid, conductivity sensors to measure conductivity of the printer fluid, volume sensors to measure a volume of the printer fluid within a receptacle, and light sensors to measure optical properties of the printer fluid. Readings from such sensors can be used to determine whether the printer fluid is appropriate for use in a printer or other appliance. For example, printer fluid that is stored at too high of a temperature may result in undesirable printing performance. Readings from a light sensor can, for example, be used to determine a density of the printer medium based on solid contents within a carrier fluid of the printer medium. Based on readings from one or more sensors, an appliance can alert an operator of undesirable conditions, and in some appliances can automatically take corrective action to adjust properties of the printer medium.

BRIEF DESCRIPTION OF THE DRAWINGS

For a detailed description of various examples, reference will now be made to the accompanying drawings in which:

FIG. 10 illustrates a bottom view of the example apparatus of FIG. 9 in a first state.

FIG. 11 illustrates a bottom view of the example apparatus of FIG. 9 in a second state.

FIG. 12 illustrates a bottom view of the example apparatus of FIG. 9 in a third state.

NOTATION AND NOMENCLATURE

In the following discussion and in the claims, the terms "including" and "comprising" are used in an open-ended fashion, and thus should be interpreted to mean "including, but not limited to . . . " Also, the term "couple" or "couples" is intended to include suitable indirect and/or direct connections. Thus, if a first component is described as being coupled to a second component, that coupling may, for example, be: (1) through a direct electrical or mechanical connection, (2) through an indirect electrical or mechanical connection via other devices and connections, and/or (3) through another suitable coupling.

DETAILED DESCRIPTION

The following discussion is directed to various examples and implementations of the disclosure. Although one or more of these examples and implementations may be preferred, the examples disclosed should not be interpreted, or otherwise used, as limiting the scope of the disclosure, including the claims. In addition, one skilled in the art will understand that the following description has broad application, and the discussion of any example is meant only to be descriptive of that example, and not intended to intimate that the scope of the disclosure, including the claims, is limited to that example.

As described above, readings from light sensors can be used to measure or calculate properties of printer fluid, such as a density of the printer medium based on optical properties of solid contents within a carrier fluid of the printer medium. In some circumstances, printer fluid can accumulate on one or more components, such as the light sensor itself, a light transmitter, or another component, and can thereby cause misrepresentation of optical properties of the printer fluid. This can in some circumstances result in inaccurate calculations relating to properties of the printer fluid (such as inaccurate density calculations). Ambient conditions of the apparatus, such as ambient temperature and brightness can also affect such measurements and related calculations. Moreover, other changes to components can affect measurement quality, such as a faulty light transmitter that outputs less light than expected.

Certain implementations described herein can provide a self-cleaning and self-calibrating apparatus that can provide more accurate and consistent sensor readings. It is appreciated that implementations described herein may include additional or an alternative advantages. Some example implementations are in the form of an apparatus that include a light transmitter, a light sensor, and an impeller. The impeller can, for example, include a blade at least a portion of which is translucent to permit calibration of a light sensor, light transmitter, or another component based on a comparison of light sensor readings when the blade is between the light transmitter and light sensor and light sensor readings when the blade is not between the light transmitter and light sensor.

Figure 1:
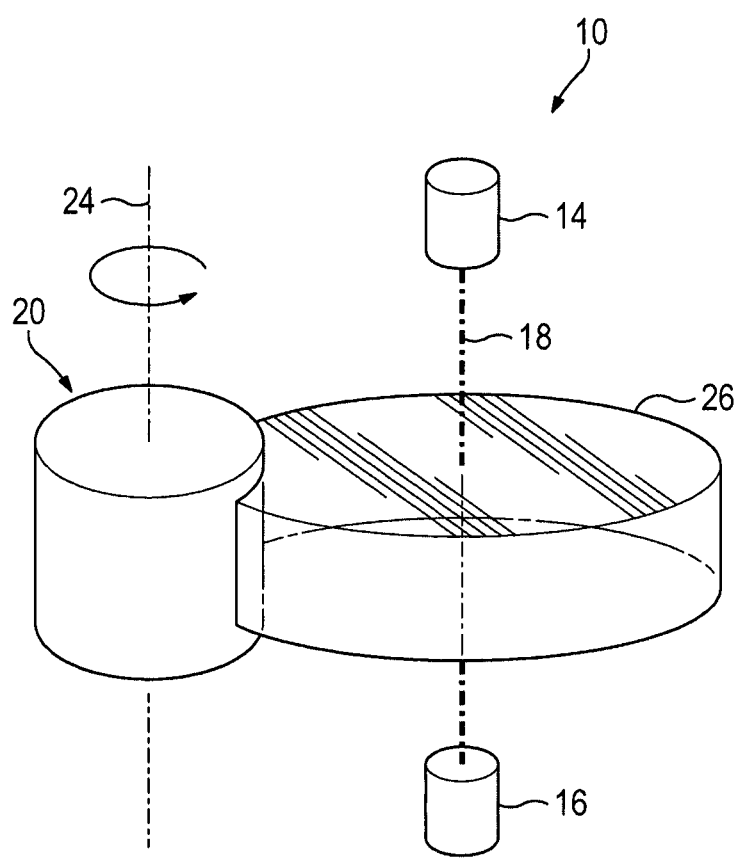
FIG. 1 illustrates a front perspective view of an apparatus, according to an example.

FIG. 1 illustrates an apparatus 10 according to an example. As described in further detail below, apparatus 10 includes a light transmitter 14, a light sensor 16 aligned along a light transmittance axis 18 of light transmitter 14, and an impeller 20 positioned between light transmitter 14 and light sensor 16. The various component of apparatus 10 are described in further detail below.

Light transmitter 14 can, for example, be in the form of any component or device that emits visible light to allow calculation of optical properties of printer fluid. In some implementations, light transmitter 14 can be designed to emit light outside of the visible spectrum, such as infrared light for example, for use in calculating other properties of printer fluid. The term "printer fluid" can, for example, refer to printer ink as well as suitable non-ink fluids. For example, printer fluid can, for example, include a pre-conditioner, gloss, a curing agent, colored inks, grey ink, black ink, metallic ink, optimizers and the like. Inkjet inks can be water based inks, latex inks or the like. In some implementations, the printer fluid can be in the form of aqueous or solvent printing fluid. Suitable printer fluid can include black, cyan, magenta, yellow, or any other suitable color for using in an inkjet printer. The term "printer" as used herein can, for example, refer to both standalone printers as well as other machines capability of printing. For example, the term "printer" as used herein can refer to an all-in-one device that provides printing as well as non-printing functionality, such as a combination printer, scanner, and fax machine.

In some implementations, light transmitter 14 is in the form of a light-emitting diode (LED). Light transmitter 14 can transmit any suitable color of visible light. For example, in some implementations, light transmitter 14 is in the form of a white LED selected to produce a minimum luminous flux at about 350 milliamperes (mA) from about 85 lumens (lm) to about 130 lm. Light transmitter 14 can be powered by a power source and can be electrically connected to the power source via physical wires, a wireless connection, or another suitable electrical path. In some implementations, light transmitter 14 is soldered to an electrical path connected to the power source. In some implementation, light transmitter 14 can be connected to a controller to control output of light transmitter 14 based on a predetermined schedule and/or feedback from another component of apparatus 10, such as light sensor 16. For example, during a calibration process, output from light transmitter 14 can be varied according to one or more calibration values. It is appreciated that light transmitter 14 and other components of apparatus 10 such as light sensor 16 and impeller 20 can be powered via a common power source.

Light sensor 16 can, for example, be used to measure visible light absorption of a printer fluid between light transmitter 14 and light sensor 16. Light sensor 16 is positioned a distance from light transmitter 14 along light transmittance axis 18 at a suitable distance based on various properties of apparatus 10, such as a properties of light transmitter 14 and light sensor 16, as well as environment properties such as, such as optical properties of the print media and the material of various components of apparatus 10, etc. As used herein, the term "light transmittance axis" can, for example, refer to a straight light transmittance path between light transmitter 14 and light sensor 16, or some other light path for light between light transmitter 14 and light sensor 16. For example, in some implementations, light from light transmitter 14 can be reflected (e.g., off a mirror or other reflective body) in order to reach light sensor 16. As another example, in some implementations, light from light transmitter 14 can be curved based on optical properties of components of apparatus 10, the printer fluid, etc.

In some implementations, light sensor 16 can be designed to detect light outside of the visible spectrum, such as infrared light for example, for use in calculating other properties of printer fluid. Light sensor 16 can contain one or more optical filters and may have a large or small surface area. Light sensor 16 can, in some implementations, be in the form of any sensor to detect visible light. For example, in some implementations, light sensor 16 can be in the form of a photodiode that converts light into current, such as a Silicon PIN photodiode. Likewise, in some implementations, light sensor 16 can be in the form of an image sensor, such as for example a semiconductor charge-coupled device (CCD) or active pixel sensors in complementary metal-oxide-semiconductor (CMOS), to convert an optical image into an electronic signal.

Impeller 20 can, for example, be in the form of a rotor that can be rotated around rotational axis 24 to increase or decrease the pressure and flow of printer fluid between light transmitter 14 and light sensor 16. Impeller 20 can, for example, include one or more blades, such as blade 26 that is positioned to rotate around rotational axis 24 and pass through light transmittance axis 18 during rotation of impeller 20 for each revolution of impeller 20. In some implementations, rotational axis 24 of impeller 20 is parallel to light transmittance axis 18. In some implementations, rotational axis 24 of impeller 20 is at an angle relative to light transmittance axis 18 that nevertheless allows impeller 20 to pass between light transmitter 14 and light sensor 16.

Impeller 20 can be rotated at any suitable speed based on various aspects of apparatus 10, printer fluid, or other conditions. In some implementations, impeller 20 is to be rotated at approximately 7200 revolutions per minute (RPM). In some implementations, impeller 20 is to be rotated at a slower or faster speed. In some implementations, impeller 20 is to be rotated at a varying speed. As but one example, impeller 20 can be programmed to run at a first speed for a first period of time and to run at a second speed at a second period of time. In some implementations, the speed of impeller 20 can, for example, be based on feedback from light sensor 16 or another component of apparatus 10, and/or can be manually controlled by an operator.

In some implementations, impeller 20 can be designed to flow printer fluid past light transmitter 14 and light sensor 16. In some implementations of apparatus 10 (such as for example the apparatus illustrated in FIG. 2 and described below), blade 26 of impeller 20 can be designed to block all printer fluid from between light transmitter 14 and light sensor 16 when blade 26 is between light transmitter 14 and light sensor 26, whereas in other implementations (such as for example the apparatus illustrated in FIG. 1), blade 26 can allow room for printer fluid or other mediums, such as air or water to flow between light transmitter 14 and blade 26 and/or light sensor 16 and blade 26.

At least a portion of blade 26 is translucent to permit calibration of light sensor 16, light transmitter 14, or another component of apparatus 10 based on a comparison of a first light sensor reading when blade 26 intersects light transmittance axis 18 and a second light sensor reading when blade 26 does not intersect light transmittance axis 18. Although it is appreciated that many materials may have some level of translucency, as used herein, the term "translucent to permit" and other similar terms are intended to refer to a reference translucency that can be used by an operator or another entity to calibrate light sensor 16, light transmitter 14, or another component of apparatus 10 based on one or more sensor readings. For example, an impeller having a completely transparent or semi-transparent blade may be suitable for calibration, whereas an impeller having a completely opaque blade would pass no light therethrough and would not be suitable for calibration. Similarly, impellers with blades having non uniform properties (e.g., certain non-uniform translucencies or cross-sections) along light transmittance axis 18 may provide errant light sensor readings not suitable for calibration. As such, in some implementations (shown for example in FIG. 1), blade 26 includes substantially flat surfaces perpendicular to light transmittance axis 18 and facing light transmitter 14 and light sensor 16. Blade 26 further includes uniform optical properties at a portion of blade 26 that passes through light transmittance axis 18. Although the translucency of blade 26 need not be known prior to recording readings from light sensor 16, the translucency of blade 26 should be determined (either as an absolute value or a reference value) in order to calibrate light sensor 16, light transmitter 14, or another component of apparatus 10. For example, in some implementations, the actual translucency value of blade 26 can be measured and used for calibration. In some implementations, blade 26 can be compared with a reference material or object having a known translucency for calibration.

In some implementations, impeller 20 includes multiple blades with different properties. For example, in some implementations, a first blade has a first translucency to permit calibration and a second blade has a second translucency to permit calibration. As another example, in some implementations (e.g., the implementation of apparatus 10 in FIG. 2 and described below), impeller 20 includes a first blade having a first shape and a second blade having a second shape. The use of multiple blades having different properties can, for example, allow for calibration under different settings or conditions.

Several examples of apparatus 10 herein refer to a single light transmitter 14, a single light sensor 16, a single impeller 20, a single blade 26, etc. However, it is appreciated that in some implementations, apparatus 10 can include multiple light transmitters 14, multiple light sensors 16, multiple impellers 20, and multiple blades 26. For example, apparatus can include a first light transmitter 14 and corresponding light sensor 16 at a first location and a second light transmitter 14 and corresponding light sensor 16 at a second location. Likewise, apparatus 10 can include a first impeller located at a first vertical position along rotational axis 24 and at a second vertical position along rotational axis 24. Similarly, in some implementations, apparatus 10 can include a first impeller 20 having a first rotational axis 24 and a second impeller 20 having a second rotational axis parallel or skewed from rotational axis 24 such that respective blades of each impeller pass between light transmitter 14 and light sensor 16 at the same time or at different times.

Figure 2:
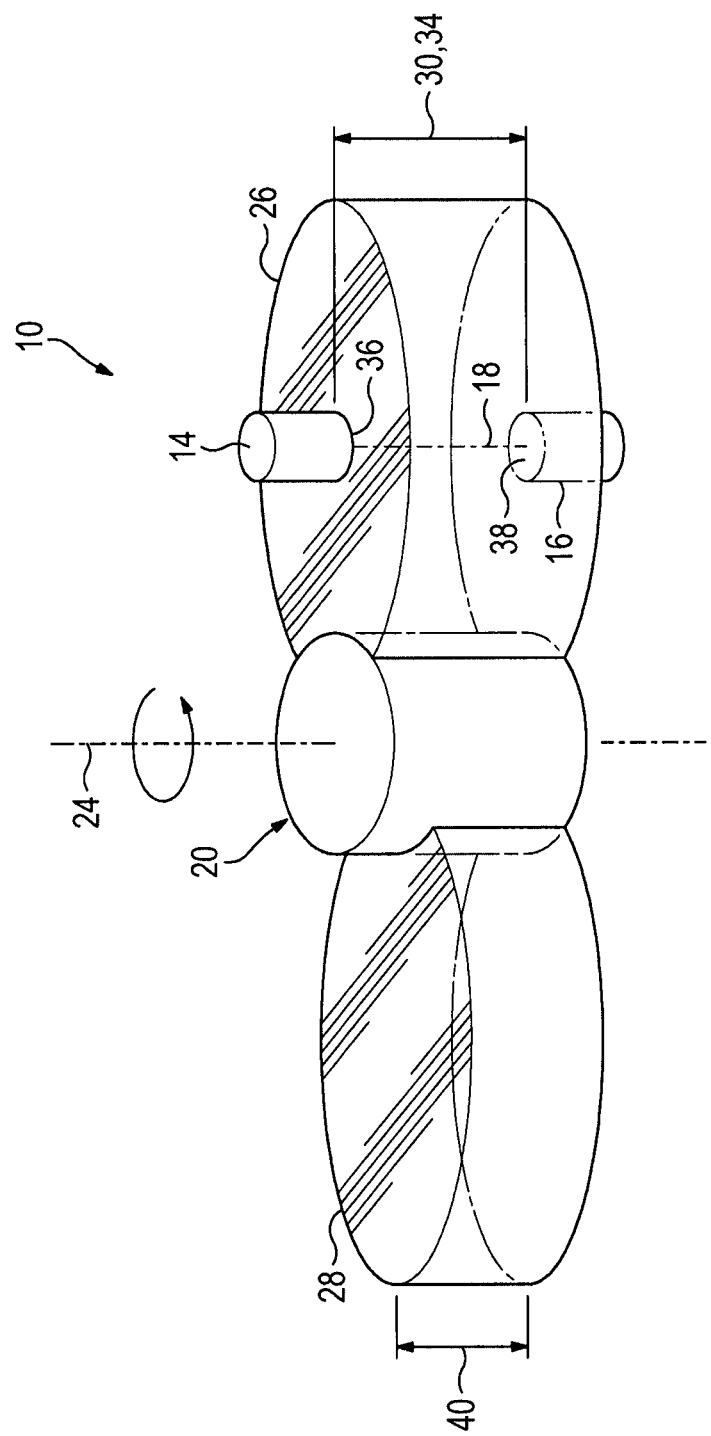
FIG. 2 illustrates a front perspective view of an apparatus in a first state, according to another example.
Figure 3:
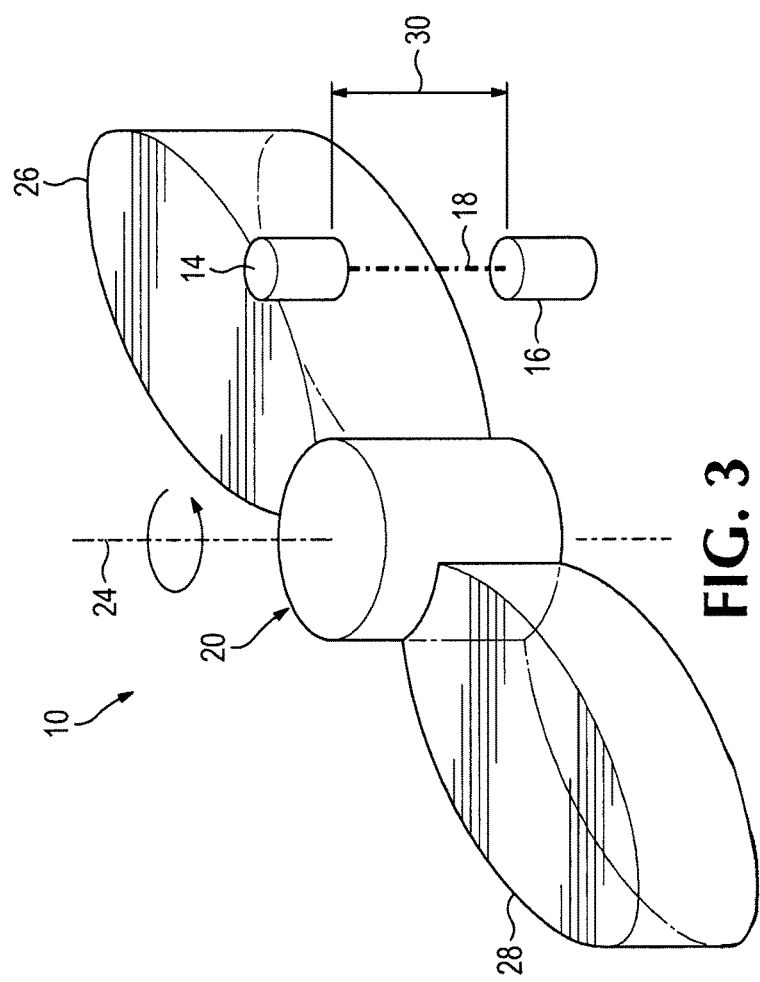
FIG. 3 illustrates a front perspective view of the example apparatus of FIG. 2 in a second state.
Figure 4:
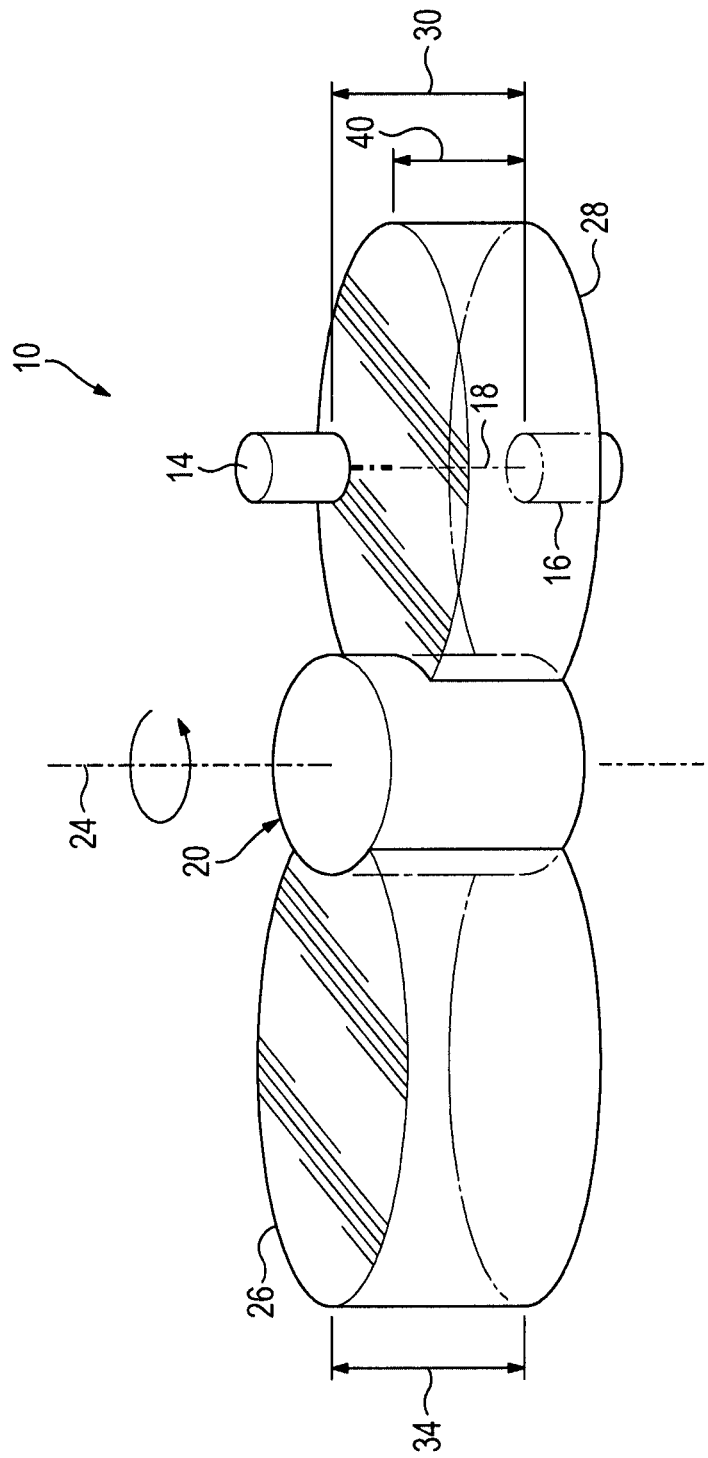
FIG. 4 illustrates a front perspective view of the example apparatus of FIG. 2 in a third state.

FIGS. 2-4 illustrate another example of apparatus 10 in various states. As described in further detail below, impeller 20 includes a first blade 26 to pass through light transmittance axis 18 during a first portion of a revolution of impeller 20 and a second blade 28 to pass through light transmittance axis 18 during a second portion of the revolution of impeller 20. FIG. 2 depicts apparatus 10 in a first state in which first blade 26 completely blocks a gap 30 between light transmitter 14 and light sensor 16, FIG. 3 depicts apparatus 10 in a second state in which neither first blade 26 nor second blade 28 are between light transmitter 14 and light sensor 16, thereby completely revealing gap 30, and FIG. 4 depicts apparatus 10 in a third state in which second blade 28 is positioned between light transmitter 14 and light sensor 16 to partially reveal gap 30. For illustration, various aspects of the apparatus of FIGS. 2-4 are referred to with respect to the apparatus of FIG. 1 and common reference numbers are used between the figures. However, it is appreciated that the use of common reference numbers are for illustration and are not intended to suggest that one or more aspects of the various apparatuses described herein are required in every implementation described herein. Moreover, suitable aspects of the apparatus of FIGS. 2-4 can be implemented in the various other apparatuses described herein and vice versa.

In the implementation of apparatus 10 depicted in FIGS. 2-4, and as specifically depicted in FIG. 2, first blade 26 includes a portion having a thickness 34 substantially equal to the thickness of gap 30 between light transmitter 14 and light sensor 16 so as to wipe an outer surface 36 of light transmitter 14 and an outer surface 38 of light sensor 16 as first blade 26 passes through light transmittance axis 18. In some implementations, gap 30 can be approximately 1 millimeter. It is appreciated that the thickness of gap 30 and the thickness 34 of first blade 26 can be selected based on various properties of apparatus 10, components thereof, or other conditions. Examples of such properties or conditions can include, for example, the sensitivity of light sensor 16, the power of light transmitter 14, the type of printer fluid used, etc.

In the implementation of apparatus 10 depicted in FIGS. 2-4 and as specifically illustrated in FIG. 4, second blade 28 includes at least a portion having a thickness 40 substantially less than the thickness of gap 30 between light transmitter 14 and light sensor 16 so as to allow printer fluid to be positioned between light transmitter 14 and light sensor 16 as second blade 28 passes through light transmittance axis 18. The implementation of second blade 28 depicted in FIGS. 2-4 has a uniform thickness 40, however it is appreciated that in some implementations of apparatus 10 (e.g., the implementation depicted in FIG. 8), second blade 28 can have a stepped thickness or some other suitable non-uniform thickness that at least partially reveals gap 30 between light transmitter 14 and light sensor 16 to allow air, printer fluid, or another fluid to flow between light transmitter 14 and second blade 28 and/or light sensor 16 and second blade 28. In some implementations, the thickness of gap 30 is approximately 1 millimeter and the thickness 40 of the portion of second blade 28 positioned to align along light transmittance axis 18 is approximately 0.8 millimeters, thereby revealing approximately 0.2 millimeters of gap 30 between light transmitter 14 and light sensor 16. It is appreciated that the thickness of the portion of gap 30 revealed between light transmitter 14 and second blade 28 and/or between light sensor 16 and second blade 28 can be selected based on various properties of apparatus 10, components thereof, or other conditions. Examples of such properties or conditions can include, for example, the sensitivity of light sensor 16, the power of light transmitter 14, the type of printer fluid used, etc.

In some implementations, first blade 26 and second blade 28 are translucent to permit calibration of light sensor 16, light transmitter 14, or another component of apparatus 10 based on a comparison of a first light sensor reading when first blade 26 intersects light transmittance axis 18, a second light sensor reading when second blade 28 intersects light transmittance axis 18, and a third light sensor reading when neither first blade 26 nor second blade 28 intersect light transmittance axis 18.

As illustrated in several examples of apparatus 10 herein, in implementations where impeller 20 includes multiple blades, the blades can be uniformly distributed about rotational axis 24 of impeller 20. For example, as depicted in the implementation of FIG. 2, first blade 26 and second blade 28 are spaced approximately 180 degrees apart. It is appreciated, that multiple blades around impeller 20 can be spaced nonuniformly. For example, in implementations with two blades, the blades can be separated by approximately 35 degrees, 90 degrees, 180 degrees, or another suitable angle. As another example, in implementations of impeller 20 including four blades, the blades can be positioned approximately 90 degrees apart or at non-uniform angles, such as an angle of approximately 30 degrees between first and second blades, an angle of approximately 45 degrees between the second and third blades, an angle of 120 degrees between third and fourth blades, and an angle of 165 degrees between the fourth and first blades. In implementations where impeller 20 includes multiple blades, each blade can have a translucent portion to permit calibration of light sensor 16, light transmitter 14 or another component of apparatus 10. In other implementations, only a single blade or other subset of blades can have such a translucent portion.

As described above, first blade 26 is designed to wipe outer surface 36 of light transmitter 14 and outer surface 38 of light sensor 16 as first blade 26 passes through light transmittance axis 18. Outer surfaces 36 and 38 of light transmitter 14 and light sensor 16 can be any suitable material, such as a clear or tinted glass or plastic, that allows light transmitter 14 and light sensor 16 to work together to determine optical properties of printer fluid or other mediums. In some implementations, the material of outer surfaces 36 and 38 of light transmitter 14 and light sensor 16 can be matched with the material of one or more blades of impeller 20 so as to prevent scratching or other damage to the outer surfaces and blades. In some implementations, one or more blades of impeller 20 (e.g., first blade 26) can elastically deform as they wipe outer surfaces 36 and 38. In some implementations, outer surfaces 36 and 38 are substantially flat so as to facilitate wiping by the one or more blades of impeller 20. In other implementations outer surfaces 36 and 38 can be rounded or another suitable shape.

Figure 5:
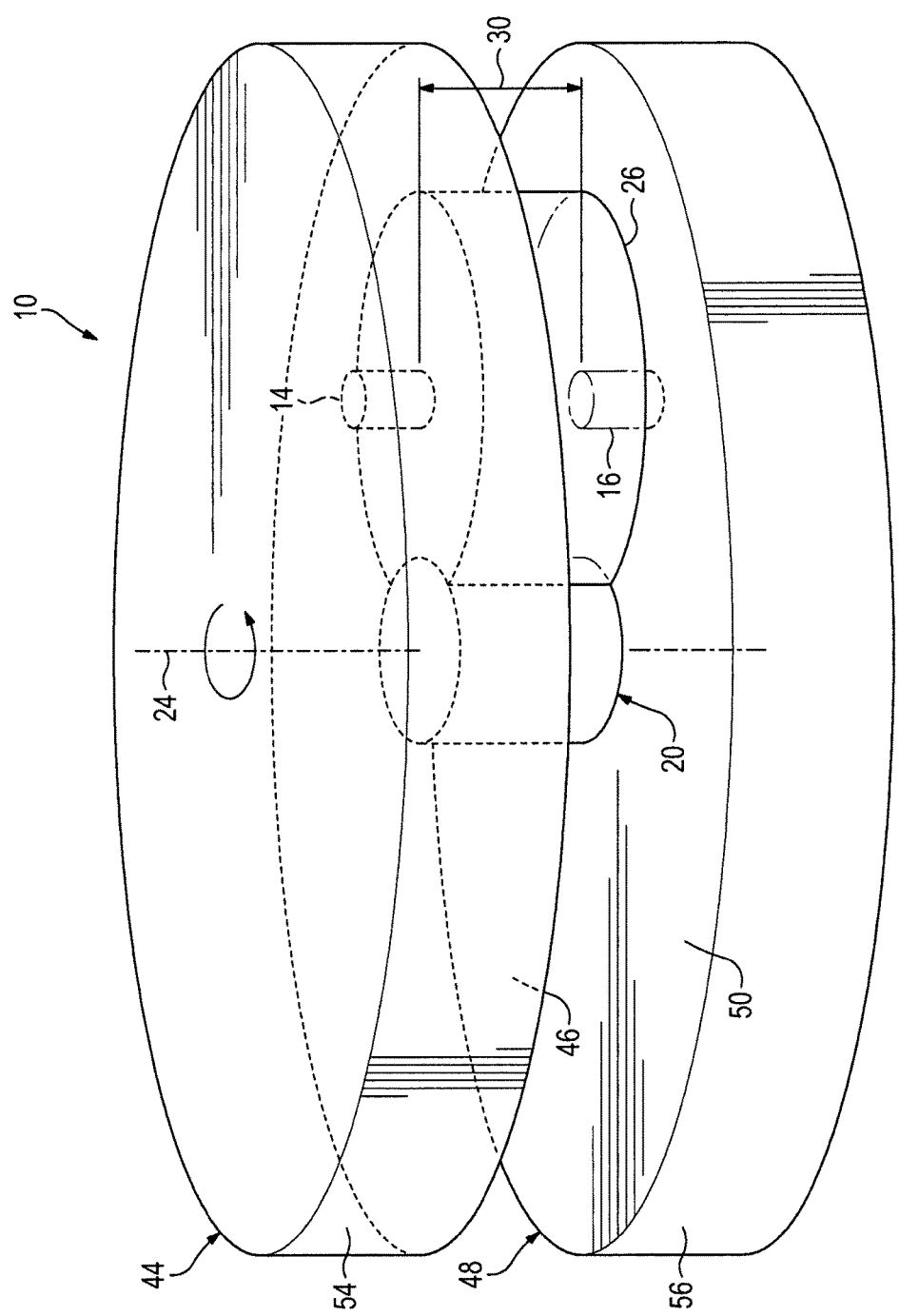
FIG. 5 illustrates a front perspective view of an apparatus, according to another example.

FIG. 5 illustrates another example apparatus 10. For illustration, various aspects of the apparatus of FIG. 5 are referred to with respect to other apparatuses described herein and common reference numbers are used between the figures. However, it is appreciated that the use of common reference numbers are for illustration and are not intended to suggest that one or more aspects of the various apparatuses described herein are required in every implementation described herein. Moreover, suitable aspects of the apparatus of FIG. 5 can be implemented in other apparatuses described herein and vice versa.

As described in further detail below, apparatus 10 of FIG. 5 includes a first plate 44 including a first surface 46, a second plate 48 including a second surface 50 substantially corresponding to first surface of first plate 44, light transmitter 14 integrated into first surface 46, light sensor 16 integrated into second surface 50 and facing light transmitter 14, and impeller 20 rotatably mounted between first surface 46 and second surface 50. The various components of this implementation of apparatus 10 will be described in further detail below.

First plate 44 and second plate 48 can, for example, be substantially uniform thin planar plates designed to receive printer fluid or other media (e.g., air, water, etc.). As illustrated in FIG. 5, first plate 44 and second plate 48 include substantially flat facing surfaces (first surface 46 and second surface 50) as well as substantially flat non-facing surfaces 54 and 56. However, it is appreciated that these surfaces can be any suitable shapes. For example, in some implementations non-facing surfaces 54 and 56 are not substantially flat. As another example, in some implementations, facing surfaces 46 and 50 are curved, for example to match a corresponding curve of blade 26 or for another purpose. In some implementations, respective outer surfaces 36 and 38 of light transmitter 14 and light sensor 16 can be substantially flush with first surface 46 of first plate 44 and second surface 50 of second plate 48. As used herein, the term "outer surface" can, for example, refer to an outer surface exposed to printer fluid, air, or another medium between first plate 44 and second plate 48. For example, in some implementations, an "outer surface" of light transmitter 14 can refer to a transparent or semi-transparent protective cover integrated with light transmitter 14. In other implementations, the term "outer surface" of light transmitter 14 can refer to a transparent or semi-transparent protective window integrated within first plate 44 through which light from light transmitter 14 is directed.

In this implementation of apparatus 10, impeller 20 includes a blade 26 to block, during a first time period, gap 30 between light transmitter 14 and light sensor 16 and to at least partially reveal, during a second time period, gap 30 to allow printer fluid or another medium between light transmitter 14 and light sensor 16. Like the implementation of the apparatus of FIGS. 1-4, blade 26 of the implementation of apparatus of FIG. 5 includes at least a portion that is translucent to permit calibration of light sensor 16 based on a comparison of a first light sensor reading during the first time period and a second light sensor reading during the second time period.

Figure 6:
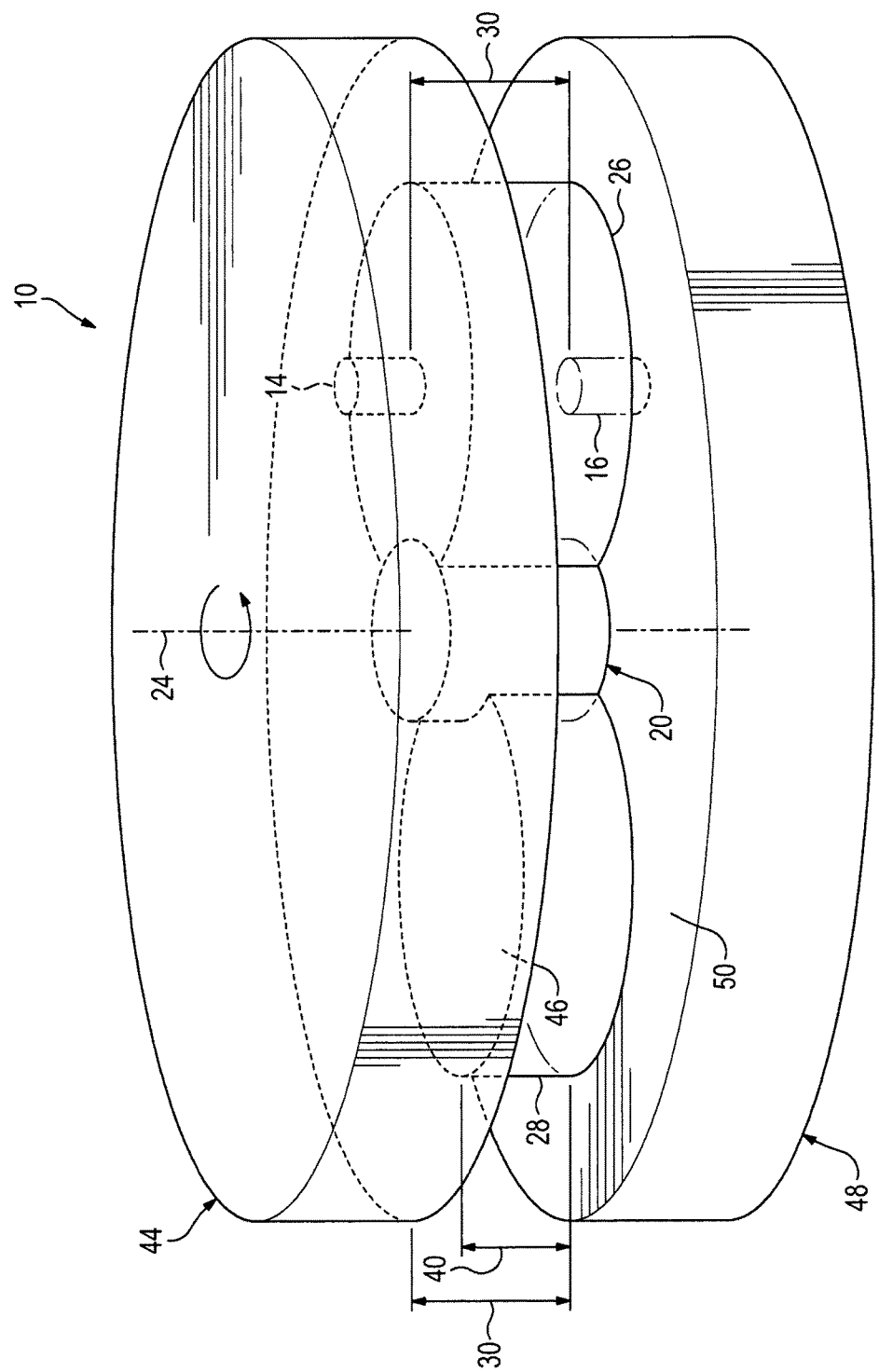
FIG. 6 illustrates a front perspective view of an apparatus, according to another example.

FIG. 6 illustrates another example apparatus 10. For illustration, various aspects of the apparatus of FIG. 6 are referred to with respect to other apparatuses described herein and common reference numbers are used between the figures. However, it is appreciated that the use of common reference numbers are for illustration and are not intended to suggest that one or more aspects of the various apparatuses described herein are required in every implementation described herein. Moreover, suitable aspects of the apparatus of FIG. 6 can be implemented in other apparatuses described herein and vice versa.

In this implementation of apparatus 10, and as depicted in FIG. 6, impeller 20 includes a first blade 26 including a portion having a thickness substantially equal to a thickness of gap 30 between light transmitter 14 and light sensor 16 so as to block, during a first time period, gap 30. Various aspects of first blade 26 of other apparatuses described herein can correspond to one or more blades of the apparatus of FIG. 6. For example, first blade 26 can be sized to wipe outer surface 36 of light transmitter 14 and outer surface 38 of light sensor 16 as first blade 26 passes between light transmitter 14 and light sensor 16.

In the implementation of apparatus 10, second blade 28 includes at least a portion substantially less than the thickness of gap 30 between light transmitter 14 and light sensor 16 to allow printer fluid, air, or another fluid to be positioned between light transmitter 14 and light sensor 16 as second blade 28 passes between light transmitter 14 and light sensor 16. As described with respect to impeller 20 of FIGS. 2-4, the implementation of second blade 28 depicted in FIG. 6 includes an entire side having a uniform thickness, however it is appreciated that in some implementations of apparatus 10 (e.g., the implementation depicted in FIG. 8), second blade 28 can have a stepped thickness or some other suitable non-uniform thickness so as to at least partially reveal gap 30 between light transmitter 14 and light sensor 16 to allow air, printer fluid, or another fluid to flow between light transmitter 14 and second blade 28 and/or light sensor 16 and second blade 28.

FIG. 5 illustrates an example system 58. For illustration, various aspects of the various apparatuses described herein are referred to with respect to system 58 and common reference numbers are used between the figures. However, it is appreciated that the use of common reference numbers are for illustration and are not intended to suggest that one or more aspects of the various apparatuses described herein are required in every implementation of system 58 described herein. Moreover, suitable aspects of system 58 can be implemented in the various apparatuses described herein and vice versa. As described in further detail below, system 58 includes a housing 60, light sensor 16 secured to housing 60, impeller 20 secured to housing 60, and a processing resource 64 in communication with light sensor 16. The various components of this implementation of system 58 will be described in further detail below.

Figure 7:
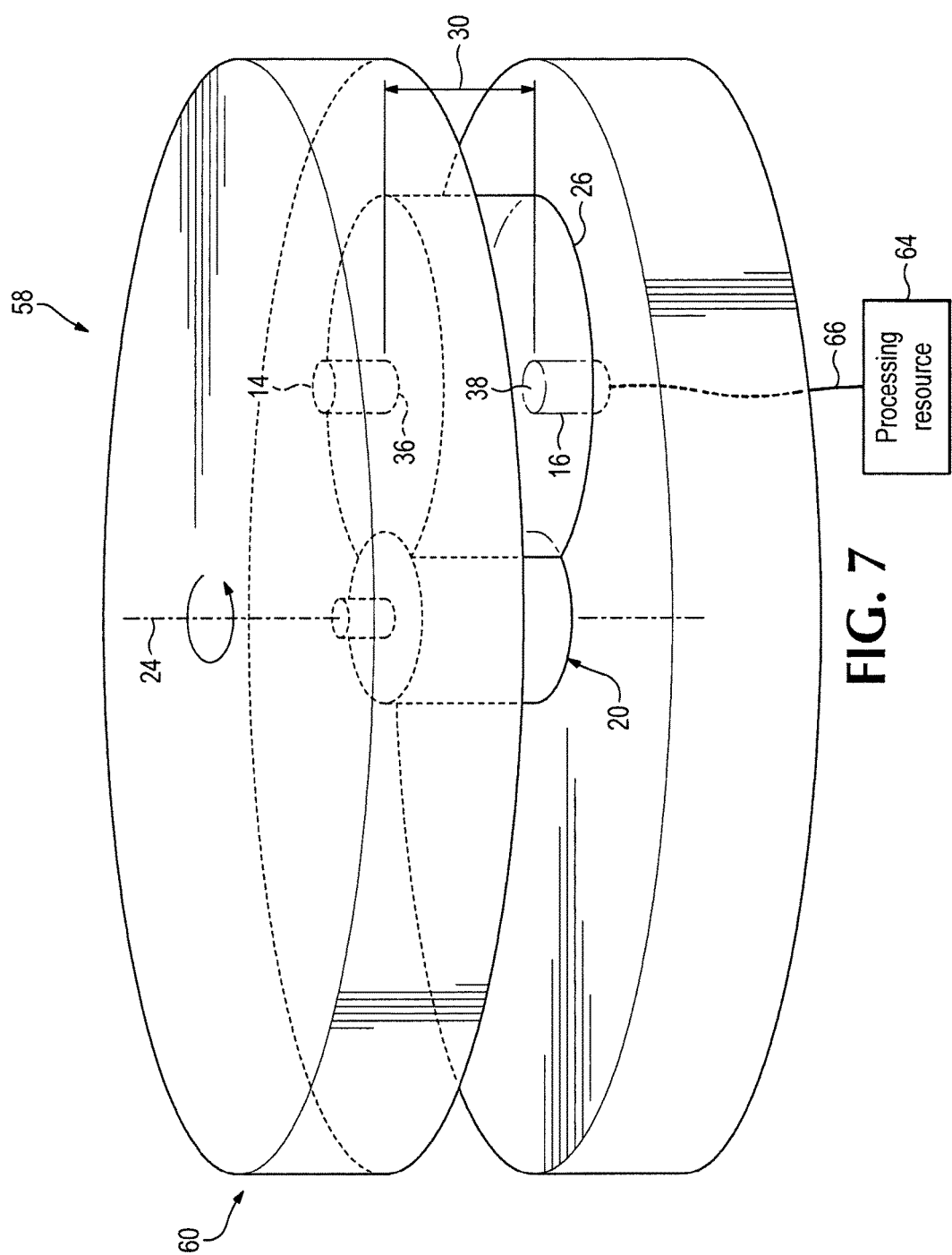
FIG. 7 illustrates a front perspective view of a system, according to another example.

Housing 60 can, for example, be designed to house and secure one or more elements of system 58, such as for example impeller 20, light transmitter 14, light sensor 16, processing resource 64, etc. Housing 60 can formed from multiple pieces or can be formed from a single piece of material. As illustrated in FIG. 7, housing 60 can be substantially cylindrical and hollow. In some implementations, housing 60 can be another suitable shape. Housing 60 can include one or more supports to assist in supporting various aspects of apparatus 10. For example, in some implementations, housing 60 can include or otherwise be attached to a spindle to rotatably secure impeller 20 along rotational axis 24. In some implementations, one or more components of system 58 can be positioned outside of housing 60. For example, in some implementations, and as shown for example in FIG. 7, processing resource 64 can be positioned external to housing 60. Housing 60 is depicted in FIG. 7 as being completely transparent so as to better illustrate various aspects of system 58. However, it is appreciated that housing 60 can be completely opaque or partially transparent.

In this implementation of system 58, impeller 20 includes a blade 26 that is rotatably mounted to housing 60 to allow blade 26 to pass between light sensor 16 and light transmitter 14 for each revolution of impeller 20. Similar to other examples of blades described herein, blade 26 of this implementation is to wipe printer fluid from outer surface 36 of light transmitter 14 and outer surface 38 of light sensor 16 as blade 26 passes between light sensor 16 and light transmitter 14. It is appreciated that various aspects of this blade can be incorporated in other blade described herein and vice versa.

Processing resource 64 of apparatus 10 is to determine a calibration setting for light sensor 16, light transmitter 14, or another component of system 58 based on received data from light sensor 16 corresponding to a first light sensor reading through blade 26 and a second light sensor reading not through blade 26. For example, the second light sensor reading can be through printer fluid, air, or another suitable medium for calibration purposes. Processing resource 64 can, for example, be used to determine a particle density value of the printer fluid based on light sensor readings. In some implementations of apparatus 10, such as that shown in FIG. 8, processing resource 64 can be coupled with a memory resource to cooperatively determining properties of printer fluid. As but one example, the particle density value of the printer fluid can be correlated to optical properties measured by light sensor 16 for a given printer fluid and other known characteristics or conditions of apparatus, such as certain ambient conditions, etc. Processing resource 64 can, for example, be connected to light sensor 16 (or another component of apparatus 10) via a signal path 66. Signal path 66 can, for example be in the form of an electrically conductive wire or another suitable path, such as an inductive or otherwise wireless data path. In some implementations, signal path 66 can pass power signals along with or instead of data signals between processing resource 64 and light sensor 16.

Figure 8:
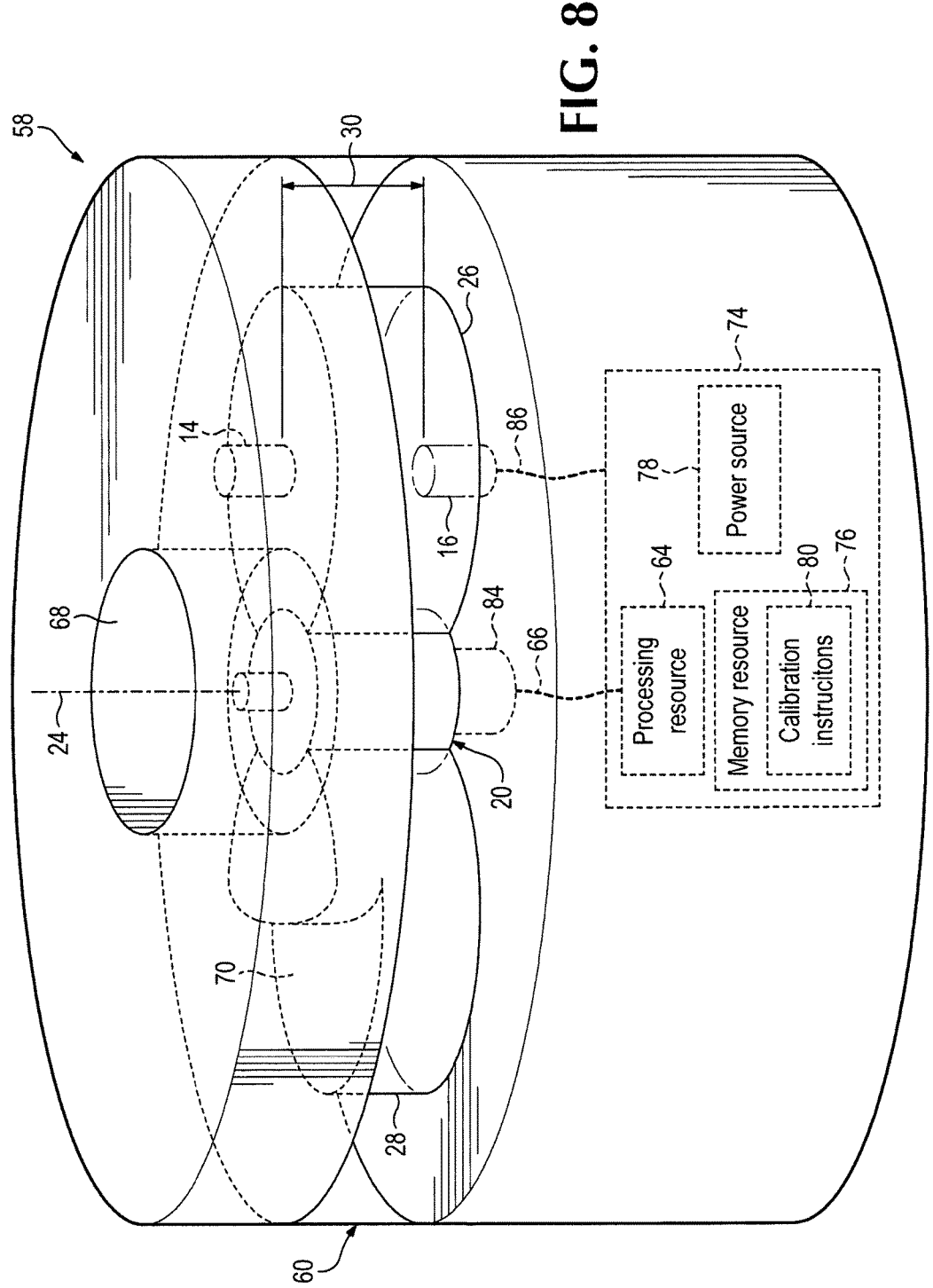
FIG. 8 illustrates a front perspective view of a system, according to another example.

FIG. 8 illustrates another example system 58. For illustration, aspects of various apparatuses and systems described herein are referred to with respect to the system of FIG. 8 and common reference numbers are used between the figures. However, it is appreciated that the use of common reference numbers are for illustration and are not intended to suggest that one or more aspects of the various apparatuses and systems described herein are required in every implementation described herein. Moreover, suitable aspects of the system of FIG. 8 can be implemented in other apparatuses and systems and vice versa.

As illustrated in FIG. 8, housing 60 can include one or more openings, such as opening 68 to allow printer fluid to enter and exit housing 60 so as to fill a space between light transmitter 14 and light sensor 16. In some implementations, such opening 68 can be positioned along a peripheral surface of housing 60. Opening 68 can also be positioned along an axial surface of housing 60 (as depicted for example in FIG. 8) or along another suitable surface of housing 60. The size and location of opening 68 can be selected based on one or more properties of system 58, components thereof, or other conditions. Examples of such properties or conditions can include, for example, the sensitivity of light sensor 16, the power of light transmitter 14, the type and viscosity of printer fluid used, etc.

In the example implementation of FIG. 8, impeller 20 includes a first blade 26 and a second blade 28 to pass between light sensor 16 and light transmitter 14 for each revolution of impeller 20. In this implementation, second blade 28 includes a recessed surface 70 to position printer fluid between light sensor 16 and light transmitter 14 as second blade 28 passes between light sensor 16 and light transmitter 14.

In the example implementation of FIG. 8, processing resource 64 is a component of a controller 74, which further includes a memory resource 76 and a power source 78. It is appreciated in that in some implementations, the various components of controller 74 can be housed within a common housing (as shown in the example of FIG. 8) or can be in separate housings connected via one or more signal paths (as shown for example in FIG. 7). As another example, in some implementations, memory resource 76 and/or processing resource 64 can be in a separate housing external of a computing device connected to system 58 via a plug or another signal path.

Suitable processing resources 64 can, for example, be in the form of a central processing unit (CPU), a semiconductor-based microprocessing resource, a digital signal processing resource (DSP) such as a digital image processing unit, other hardware devices or processing elements suitable to retrieve and execute instructions stored in a computer-readable medium, or suitable combinations thereof. Suitable processing resources can, for example, include single or multiple cores on a chip, multiple cores across multiple chips, multiple cores across multiple devices, or suitable combinations thereof. Suitable processing resources can be functional to fetch, decode, and execute instructions as described herein. As an alternative or in addition to retrieving and executing instructions, suitable processing resources can, for example, include at least one integrated circuit (IC), other control logic, other electronic circuits, or suitable combination thereof that include a number of electronic components for performing the functionality of instructions stored on a computer-readable medium. Suitable processing resources can, for example, be implemented across multiple processing units and instructions may be implemented by different processing units in different areas of controller 74.

In some implementations, memory resource 76 can store instructions for use in calibrating and controlling components of system 58. For example, in some implementations, memory resource 76 can include calibration instructions 80 for calibrating light sensor 16 based on one or more sensor readings. Suitable memory resources 76 can include any computer-readable medium for use by or in connection with an instruction execution system such as a computer/processor based system or an ASIC (Application Specific Integrated Circuit) or other system that can fetch or obtain the logic from computer-readable medium and execute the instructions contained therein. Suitable machine-readable storage mediums can, for example, be in the form of non-transitory storage mediums. The term "non-transitory" as used herein can, for example, refer to mediums that do not encompass a transitory signal but instead are made up of one or more memory resource components configured to store relevant machine-readable instructions. Such mediums can, for example, be in the form of electronic, magnetic, optical, or other physical storage mediums to store information, such as computer instructions.

As used herein, the term "machine-readable storage medium" can, for example, include Random Access Memory resource (RAM), flash memory resource, a storage drive (e.g., a hard disk), any type of storage disc (e.g., a Compact Disc Read Only Memory resource (CD-ROM), any other type of compact disc, a DVD, etc.), and the like, or a combination thereof. In some implementations, mediums can correspond to a memory resource including a main memory resource, such as a Random Access Memory resource (RAM), where software may reside during runtime, and a secondary memory resource. The secondary memory resource can, for example, include a nonvolatile memory resource where a copy of machine-readable instructions are stored. It is appreciated that instructions and data can be stored on separate machine-readable storage mediums. For purposes of clarity, multiple memory resources can be identified as a single memory resource and multiple processing resources can be identified as a single processing resource.

In some implementations, processing resource 64 can, for example, be programmed to interact with memory resource 76 to determine a calibration setting for light sensor 16 based on received data from light sensor 16 corresponding to a first light sensor reading through first blade 26, a second light sensor reading not through first blade 26 or second blade 28 (e.g., only through printer fluid, air, or another medium), and a third light sensor reading through second blade 28.

Controller 74 can include one or more connections to other components of system 58. For example, as depicted in FIG. 8, controller 74 can be connected via a first signal path 66 to a motor 84 and connected via a second signal path 86 to light sensor 16. It is appreciated that in some implementations, controller 74 can be wired or otherwise connected to light transmitter 14 as well as other components of system 58, or in some implementations, these components can be controlled by another controller or operator.

Figure 9:
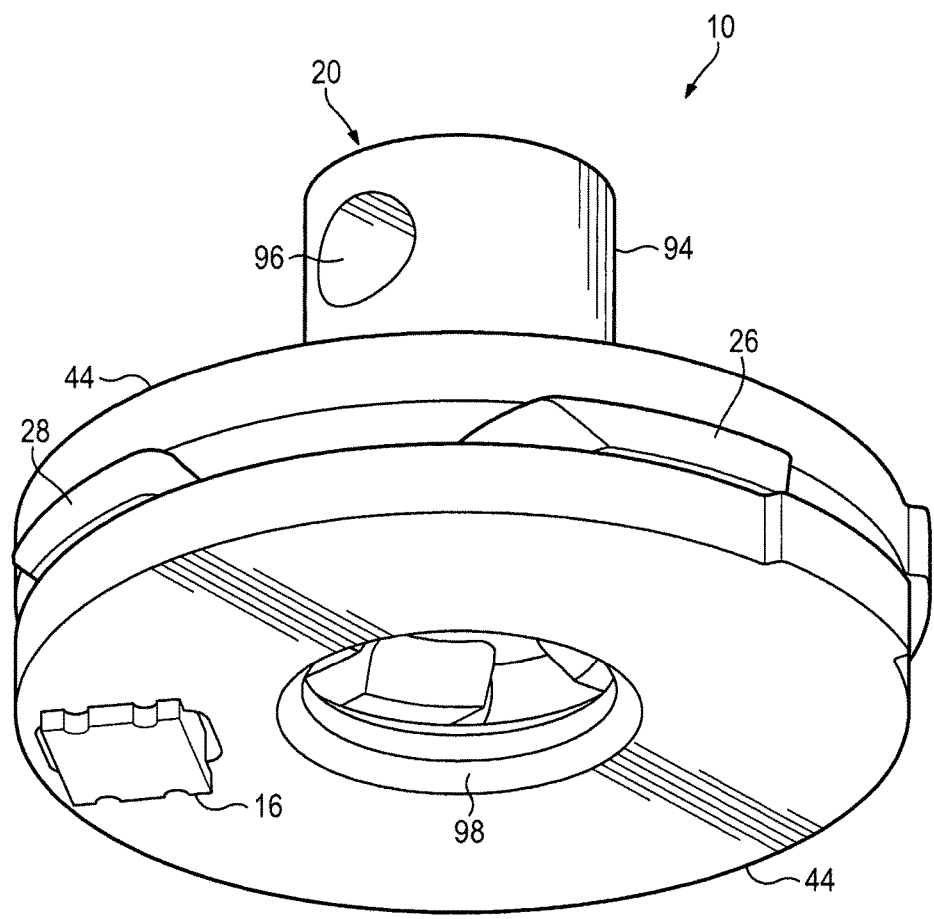
FIG. 9 illustrates a bottom perspective view of an apparatus, according to another example.
Figure 13:
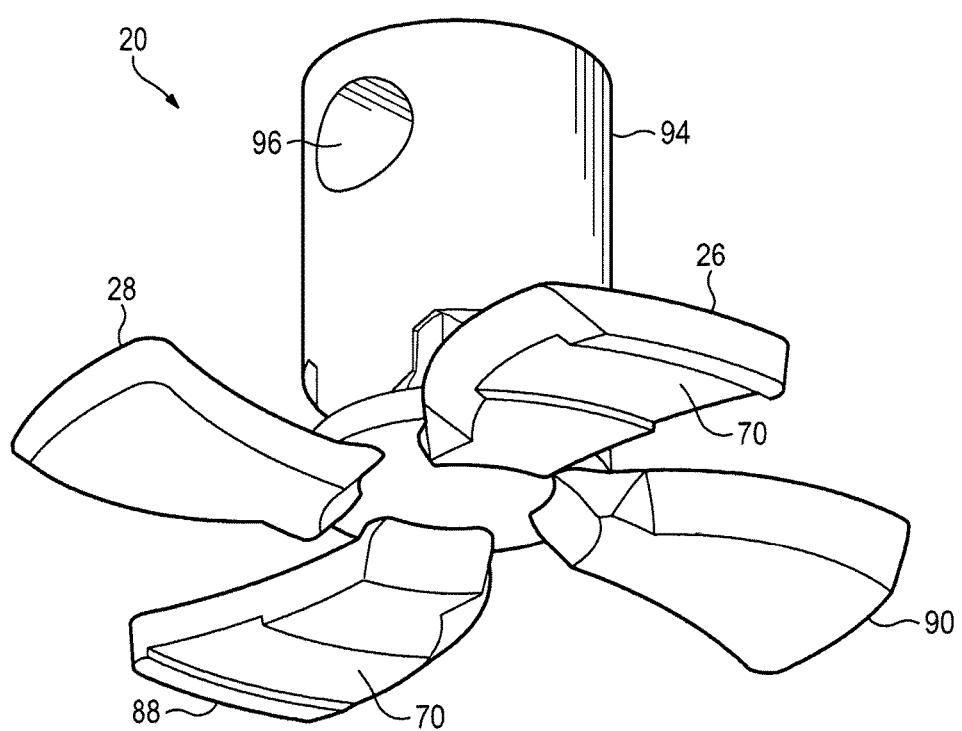
FIG. 13 illustrates a bottom perspective of an example impeller of the example apparatus of FIG. 9.

FIGS. 9-13 illustrate various views of another example apparatus 10 and impeller 20 having first, second, third, and fourth blades 26, 28, 88, and 90 in various states (fourth blade 90 is not visible in FIG. 9). In particular, FIG. 9 illustrates a bottom perspective view of the example apparatus, FIG. 10 illustrates a bottom view of the example apparatus in a first state in which no blade is between light sensor 16 and light transmitter 14 (light transmitter 14 is not visible in FIG. 10), FIG. 11 illustrates a bottom view of the example apparatus in a second state in which a partially recessed third blade 88 is between light sensor 16 and light transmitter 14 (light transmitter 14 is not visible in FIG. 11), FIG. 12 illustrates a bottom view of the example apparatus in a third state in which second blade 28 is between light sensor 16 and light transmitter 14 (light transmitter 14 is not visible in FIG. 12), and FIG. 13 illustrates a perspective view of impeller 20 of the apparatus of FIGS. 9-12. Various aspects of the apparatus are removed for illustration in certain figures, such as for example second plate 48 in FIGS. 10-12. For illustration, various aspects of other apparatuses described herein are referred to with respect to the apparatus of FIGS. 9-13 and common reference numbers are used between the figures. However, it is appreciated that the use of common reference numbers are for illustration and are not intended to suggest that one or more aspects of the various apparatuses described herein are required in every implementation described herein. Moreover, suitable aspects of the various apparatuses and systems described herein can be implemented in the apparatus of FIGS. 9-13 and vice versa.

As shown in FIGS. 9-13, impeller 20 includes an impeller shaft 94 with a peripheral opening 96 to allow printer fluid to flow between first plate 44 and second plate 48. Likewise, first plate 44 and second plate 48 include respective openings 98 (opening of first plate 44 is not visible in FIG. 9), to allow printer fluid to enter through first plate 44 and exit through second plate 48. In addition, and as shown for example in FIG. 13, first blade 26 and third blade 88 include recessed surfaces 70, whereas second blade 28 and fourth blade 90 are substantially uniform. It is appreciated that the exact shape of impeller 20 or other aspects of the apparatus of FIGS. 9-12 can be incorporated in other apparatuses or systems described herein.

Figure 14:
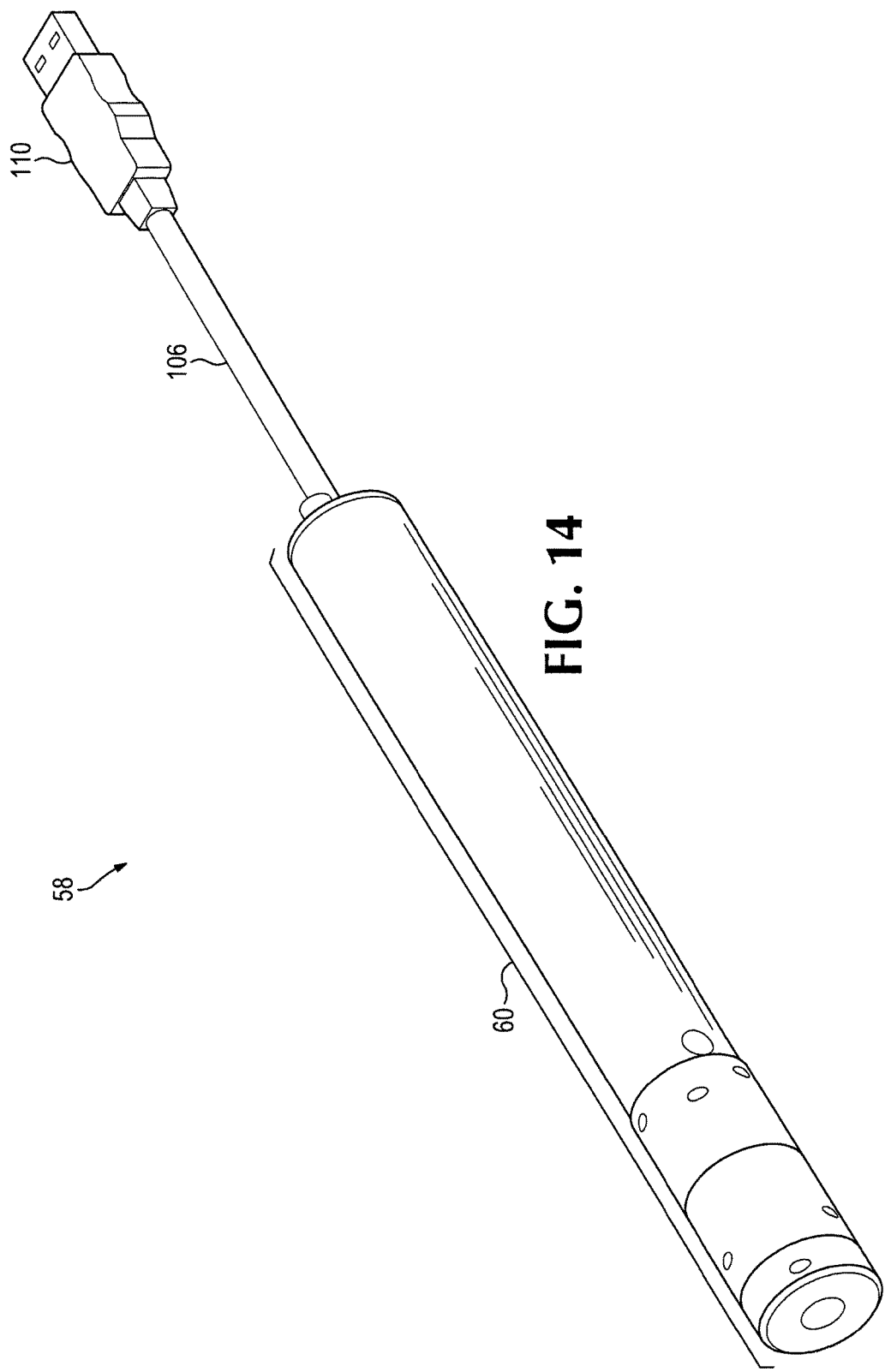
FIG. 14 illustrates a front perspective view of a system, according to another example.
Figure 15:
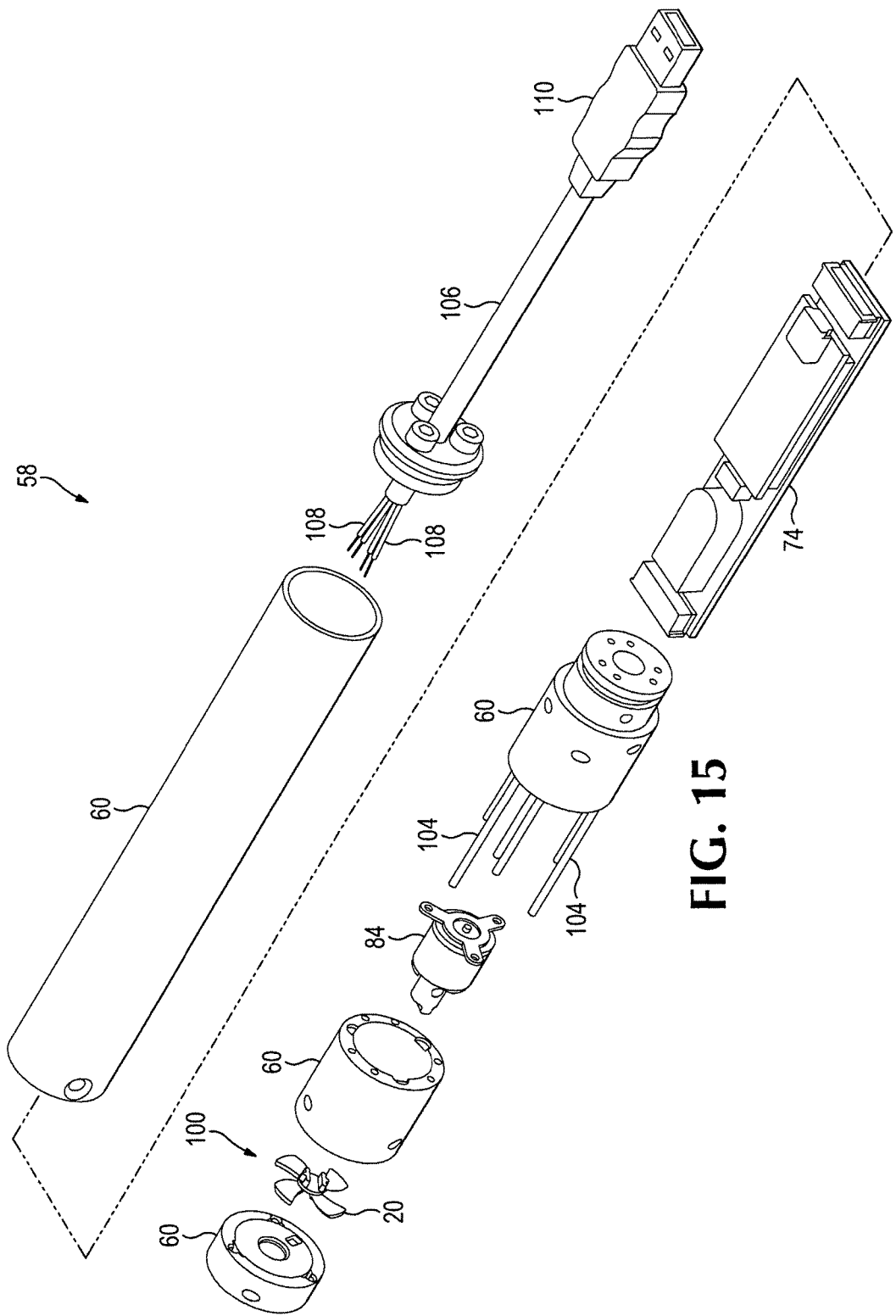
FIG. 15 illustrates an exploded view of the example system of FIG. 14.

FIGS. 14-15 illustrates a system 58 incorporating the apparatus of FIGS. 9-12. In particular, FIG. 14 depicts a perspective view of an assembled system 58 and FIG. 15 depicts an exploded view of system 58. As shown in FIGS. 14-15, system 58 includes housing 60 (separated into four pieces), a sensor assembly 100 (including light transmitter 14, light sensor 16, and impeller 20), motor 84, various structural supports 104, controller 74, and a cable 106 including plug 110 and leads 108 (not visible in FIG. 13) for connecting to controller 74 to cable 106. For illustration, various aspects of other apparatuses and systems described herein are referred to with respect to the system of FIGS. 14-15 and common reference numbers are used between various figures. However, it is appreciated that the use of common reference numbers are for illustration and are not intended to suggest that one or more aspects of the various apparatuses described herein are required in every implementation described herein. Moreover, suitable aspects of the system of FIGS. 14-15 can be implemented in other apparatuses and systems described herein and vice versa.

In operation, system 58 can be used to calibrate components of system 58 in air or another suitable medium (e.g., water) before or after system is submerged in printer fluid to record optical properties of the printer fluid. Based on these sensor measurements, adjustments can be made for calibrating light sensor 16, light transmitter 14, or another component of system 58. In some implementations, system 58 is designed to be submerged in printer fluid and operated to record sensor measurements from sensor assembly 100 for calibration purposes.

Plug 110 can be in the form of any suitable plug for providing data and/or power signals to an external all-purpose computer, standalone server, storage device, or other computing device. For example, in some implementations (and as depicted for example in FIGS. 13-14), plug 110 can be in the form of a Universal Serial Bus (USB) plug for communicating with a corresponding USB port of a computing device. In some implementations, system 58 is wireless connectable to a computing device and does not require a plug for data communication. Moreover, in some implementations, system 58 is powered by a battery housed within housing 60 or otherwise connected to system 58. It is appreciated that data signals can be provided to a computing device to assist in calibration of components of system 58 or for other purposes. For example, in some implementations, processing resource 64 is located on an external controller 74 or external computing device and controller 74 housed within housing 60 is not used in calibration of the various components of system 58. Instead, in such an implementations, controller 74 can be used for controlling a rotational speed of impeller 20 or for controller other operations of system 58.

While certain implementations have been shown and described above, various changes in form and details may be made. For example, some features that have been described in relation to one implementation and/or process can be related to other implementations. In other words, processes, features, components, and/or properties described in relation to one implementation can be useful in other implementations. Furthermore, it should be understood that the devices described herein can include various combinations and/or sub-combinations of the components and/or features of the different implementations described. Thus, features described with reference to one or more implementations can be combined with other implementations described herein.

The above discussion is meant to be illustrative of the principles and various implementations of the present disclosure. Numerous variations and modifications will become apparent to those skilled in the art once the above disclosure is fully appreciated. It is intended that the following claims be interpreted to embrace all such variations and modifications.

What is claimed is:

1. An apparatus comprising:
   a light transmitter;
   a light sensor aligned along a light transmittance axis of the light transmitter;
   an impeller positioned between the light transmitter and the light sensor, the impeller including a blade to pass through the light transmittance axis during rotation of the impeller,
   wherein the blade is translucent to permit calibration of the light sensor based on a comparison of a first light sensor reading when the blade intersects the light transmittance axis and a second light sensor reading when the blade does not intersect the light transmittance axis,
   wherein the blade is to wipe an outside surface of the light transmitter and an outside surface of the light sensor as the blade passes through the light transmittance axis.

2. The apparatus of claim 1, wherein the light sensor is to measure light absorption of a printer fluid between the light transmitter and the light sensor.

3. The apparatus of claim 2, wherein the light sensor is to measure light absorption of printer ink between the light transmitter and the light sensor.

4. The apparatus of claim 1, wherein the blade includes a portion having a thickness substantially equal to a gap thickness between the light transmitter and the light sensor.

5. The apparatus of claim 4, wherein the gap thickness is approximately 1 millimeter.

6. The apparatus of claim 1, wherein the blade includes a portion having a thickness substantially less than a gap thickness between the light transmitter and the light sensor to allow printer fluid to be positioned between the light transmitter and the light sensor as the blade passes through the light transmittance axis.

7. The apparatus of claim 6, wherein the gap thickness is approximately 1 millimeter and the thickness of the portion is approximately 0.8 millimeters.

8. The apparatus of claim 1, wherein the impeller includes a first blade to pass through the light transmittance axis during a first portion of a revolution of the impeller and a second blade to pass through the light transmittance axis during a second portion of the revolution of the impeller, and
   wherein the first and second blades are translucent to permit calibration of the light sensor based on a comparison of a first light sensor reading when the first blade intersects the light transmittance axis, a second light sensor reading when the second blade intersects the light transmittance axis, and a third light sensor reading when neither the first blade nor the second blade intersect the light transmittance axis.

9. The apparatus of claim 8, wherein the first blade includes a portion having a thickness substantially equal to a gap thickness between the light transmitter and the light sensor so as to wipe the outside surface of the light transmitter and the light sensor as the first blade passes through the light transmittance axis, and
   wherein the second blade includes a portion having a thickness substantially less than the gap thickness to allow printer fluid to be positioned between the light transmitter and the light sensor as the second blade passes through the light transmittance axis.

10. An apparatus comprising:
    a first plate including a first surface;
    a second plate including a second surface substantially parallel to the first surface;
    a light transmitter integrated into the first surface;
    a light sensor integrated into the second surface and facing the light transmitter;
    an impeller rotatably mounted between the first surface and the second surface, the impeller including a blade to block, during a first time period, a gap between the light transmitter and the light sensor and to at least partially reveal, during a second time period, the gap between the light transmitter and the light sensor to allow printer fluid between the light transmitter and the light sensor,
    wherein the blade includes a portion that is translucent to permit calibration of the light sensor based on a comparison of a first light sensor reading during the first time period and a second light sensor reading during the second time period
    wherein the blade is to wipe printer fluid from an outer surface of the light transmitter and an outer surface of the light sensor as the blade passes between the light transmitter and the light sensor.

11. The apparatus of claim 10, wherein the blade is to completely reveal, during the second time period, the gap between the light transmitter and the light sensor.

12. The apparatus of claim 10, wherein the outer surface of the light transmitter is substantially flush with the first surface of the first plate and the outer surface of the light sensor is substantially flush with the second surface of the second plate.

\* \* \* \* \*